United States Patent
Costabile et al.

(10) Patent No.: US 10,092,403 B2
(45) Date of Patent: Oct. 9, 2018

(54) SYSTEMS AND METHODS FOR SECURELY ASSEMBLING A SPINAL IMPLANT

(71) Applicant: Alphatec Spine, Inc., Carlsbad, CA (US)

(72) Inventors: Jonathan T. Costabile, San Diego, CA (US); Nathaniel DuBois, San Marcos, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 15/296,989

(22) Filed: Oct. 18, 2016

(65) Prior Publication Data

US 2017/0105840 A1 Apr. 20, 2017

Related U.S. Application Data

(60) Provisional application No. 62/243,787, filed on Oct. 20, 2015.

(51) Int. Cl.
*A61F 2/44* (2006.01)
*A61F 2/28* (2006.01)
*A61F 2/46* (2006.01)

(52) U.S. Cl.
CPC .................. *A61F 2/28* (2013.01); *A61F 2/44* (2013.01); *A61F 2/442* (2013.01); *A61F 2/4601* (2013.01); *A61F 2002/2835* (2013.01)

(58) Field of Classification Search
CPC ............................................ A61F 2/44–2/447
See application file for complete search history.

(56) References Cited

U.S. PATENT DOCUMENTS

| | | | |
|---|---|---|---|
| 6,666,866 B2 | 12/2003 | Martz et al. | |
| 7,232,463 B2 | 6/2007 | Falahee | |
| 8,267,997 B2 | 9/2012 | Colleran | |
| 8,491,658 B1 * | 7/2013 | Etminan | A61F 2/442 623/17.16 |
| 8,932,358 B1 * | 1/2015 | Nehls | A61F 2/4455 623/17.16 |
| 2004/0127900 A1 * | 7/2004 | Konieczynski | A61B 17/8042 606/281 |
| 2007/0142841 A1 | 6/2007 | Reitzig et al. | |
| 2008/0039845 A1 * | 2/2008 | Bonutti | A61B 17/0401 606/62 |

(Continued)

OTHER PUBLICATIONS

International Search Report, dated Feb. 3, 2017, PCT/US2016/057723 filed Oct. 19, 2016.

*Primary Examiner* — Nicholas Plionis
(74) *Attorney, Agent, or Firm* — Honigman Miller Schwartz and Cohn LLP (57) ABSTRACT

Systems and methods for implanting a spinal implant between two vertebral bodies are provided. The spinal implant may include a main body adapted to rest between and adjacent to the two vertebral bodies, the main body having a cavity therein adapted to hold a filler and a cap adapted to connect to the main body where the cap is connectable after the main body has been inserted between the vertebral bodies and after the filler has been inserted into the cavity of the main body. The cap is securable to the main body by means of a securement member providing for a permanent connection between the main body and the cap.

14 Claims, 8 Drawing Sheets

(56) References Cited

U.S. PATENT DOCUMENTS

2014/0088710 A1* 3/2014 Etminan ............. A61F 2/30744
 623/17.16
2015/0100129 A1 4/2015 Waugh et al.
2015/0119992 A1 4/2015 Kirschman
2016/0015523 A1* 1/2016 Lewis ..................... A61F 2/447
 623/17.16

* cited by examiner

SYSTEMS AND METHODS FOR SECURELY ASSEMBLING A SPINAL IMPLANT

CROSS-REFERENCE TO RELATED APPLICATIONS

This application claims priority of U.S. Provisional Patent Application No. 62/243,787 filed Oct. 20, 2015, the contents of which are incorporated herein by reference.

FIELD

The present specification relates to a system and method for securing a spinal implant between two vertebral bodies and, more specifically, wherein the spinal implant is adapted to hold a filler.

BACKGROUND

Spinal implants configured to hold a filler such as a bone graft material are generally known; however, these implants require filling prior to positioning between the vertebral bodies. The filler material, such as a bone graft, is positioned on and around an implant and thereafter positioned between two vertebral bodies. This method and system frequently results in the filler material not having sufficient contact with the adjacent vertebral bodies. Some implants overcome this problem by providing a two-piece construct. A first portion may be inserted into the disc space and packed with filler. Subsequently, a second portion may then be inserted and coupled with the first portion to enclose the filler. Such a two-piece construct however may encounter difficulties of aligning the first and second portions and securing them together permanently. Accordingly, there exists a need for an alternative two-piece spinal implant allowing for the filler material to be inserted after positioning of the spinal implant and to provide consistent alignment and securement of the first and second portions. It is further desired to have a two piece spinal implant wherein the first piece is locked into place with the second piece by simply securing the first piece to the second piece by a guide wire.

SUMMARY

In one embodiment, a system for securing a spinal implant positioned between two vertebral bodies may include a main body adapted to rest between and adjacent to the two vertebral bodies. The spinal implant includes the main body (also referred to as a cage) having a top opening providing for access to a cavity of the main body. The cavity of the main body is adapted to hold a filler. The system and method includes a cap adapted to connect to the main body by closing the top opening. The cap is connectable after the main body has been inserted between the vertebral bodies and after the filler has been inserted into the cavity of the main body.

In another embodiment, a system for securing a spinal implant positioned between two vertebral bodies includes an elongated member extending from a top edge of the main body. The main body is adapted to rest between a pair of adjacent vertebral bodies. The main body includes a cavity therein adapted to hold a filler. In this embodiment the cap adapted to connect to the main body includes a through-hole wherein the cap is slidable along the elongated member vis-a-vis the through-hole. The cap may be connectable after the main body has been inserted between the vertebral bodies and after the filler has been inserted into the cavity of the main body. The cap is secured to the main body by at least one securement member so as to permanently attach the cap to the main body.

In yet another embodiment, a method for positioning a spinal implant between two vertebral bodies is provided. The method includes providing an implant having a main body, at least one elongated member extending therefrom, and a cap. The method includes the steps of inserting a main body between the two vertebral bodies, inserting a filler into the cavity within the main body, sliding the cap along the at least one elongated member until the cap reaches the main body, and securing the cap to the main body.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION OF THE INVENTION

A system for implanting a spinal implant includes a spinal implant having a main body. The main body may be general U-shaped having a pair of legs, a front edge and a top opening. The inferior and superior surfaces of the legs may be ribbed. The system includes at least one elongated member which may be inserted into an aperture disposed on a top end of one of the pair of legs. The system includes a cap configured to connect to the main body and tightly secured to the main body. The main body is positioned between a pair of vertebral bodies where the ribbed inferior and superior surfaces of the legs rest directly adjacent to and touch the respective inferior and superior surfaces of the vertebral bodies. As used herein, the superior surface refers to the surface of the vertebral body which faces the head of a user and the inferior surface refers to the surface of the vertebral body which faces the feet of the user.

The main body is inserted between the two vertebral bodies such that the top opening is exposed. The main body may be inserted with the elongated member mounted to the aperture during the insertion or after. After the main body is inserted between the vertebral bodies, a filler, such as a bone graft material, is inserted into a cavity of the main body. After the filler has been installed, the cap slides along the elongated member and pressed into the aperture generating a pinch fit engagement with the elongated member within the aperture so as to secure the cap to the main body. After the cap is secured to the main body the elongated member may be broken off so as to be disconnected from the main body.

Figure 1:
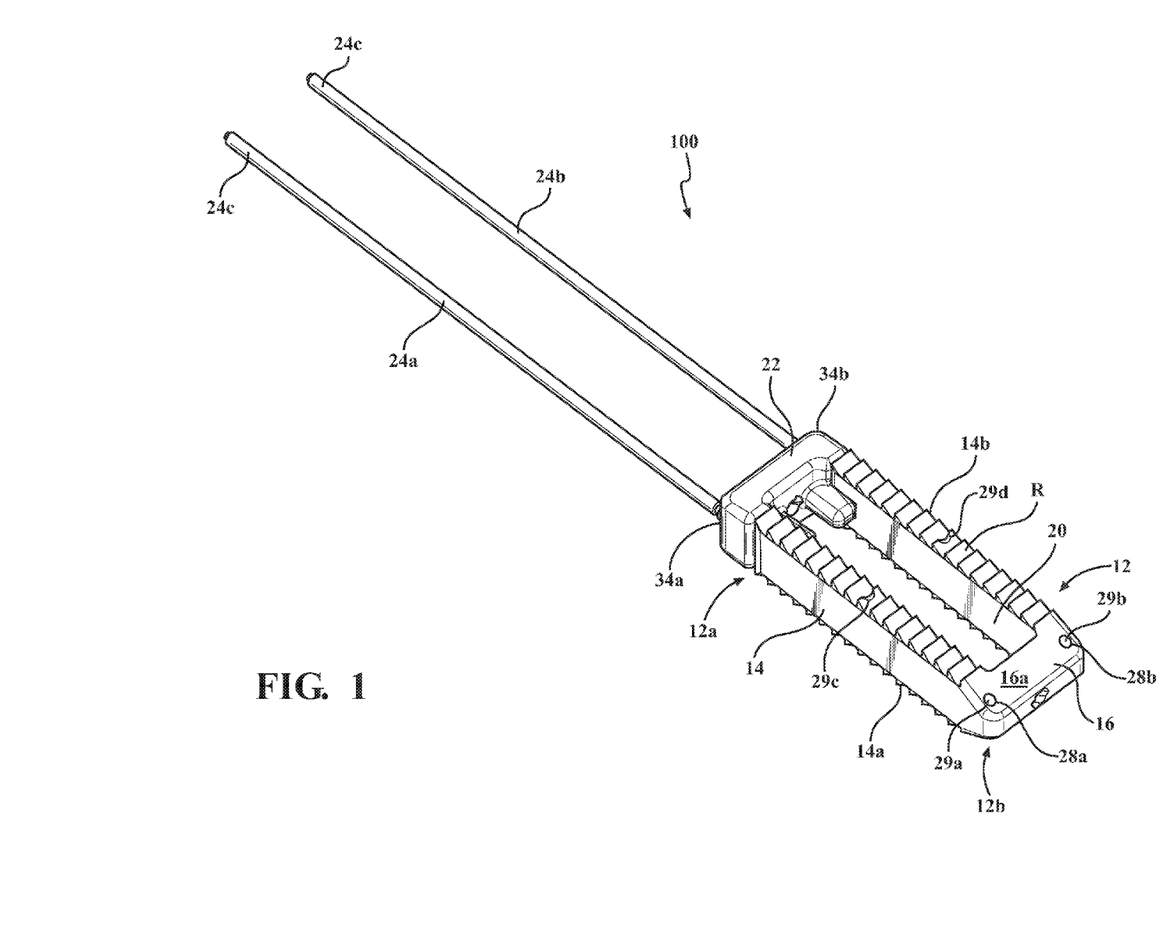
FIG. 1 depicts a perspective view of the spinal implant according to one or more of the embodiments shown and described herein.
Figure 2:
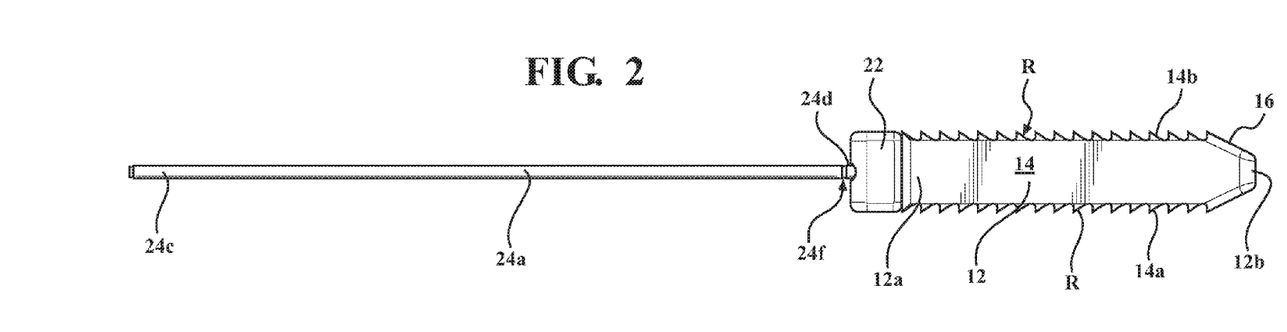
FIG. 2 illustrates a side view of the spinal implant according to one or more embodiments shown and described herein.
Figure 3:
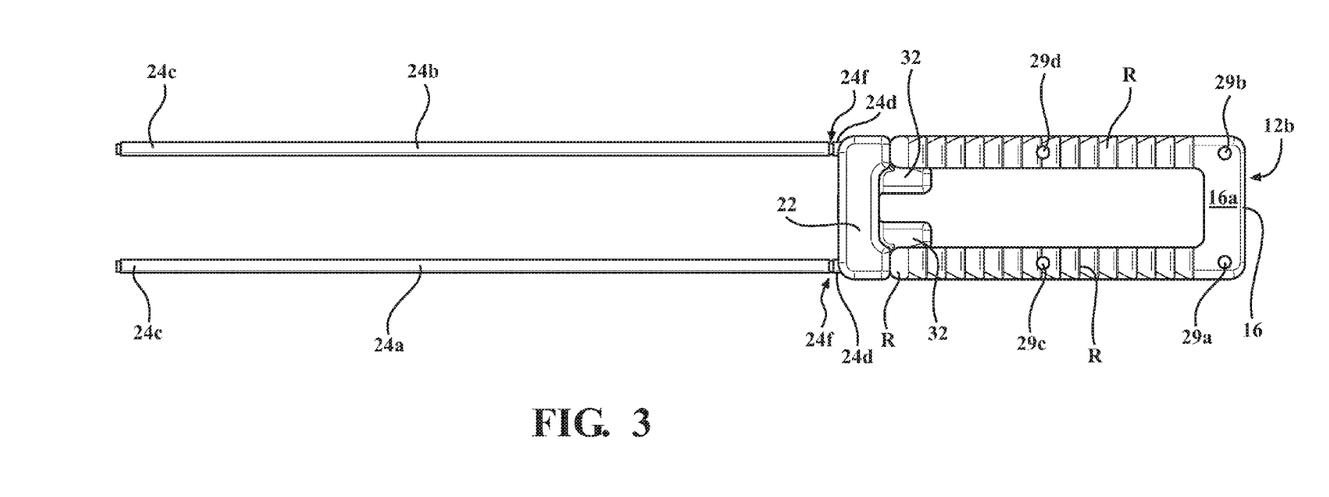
FIG. 3 depicts a top view of the spinal implant according to one or more embodiments shown and described herein.
Figure 4:
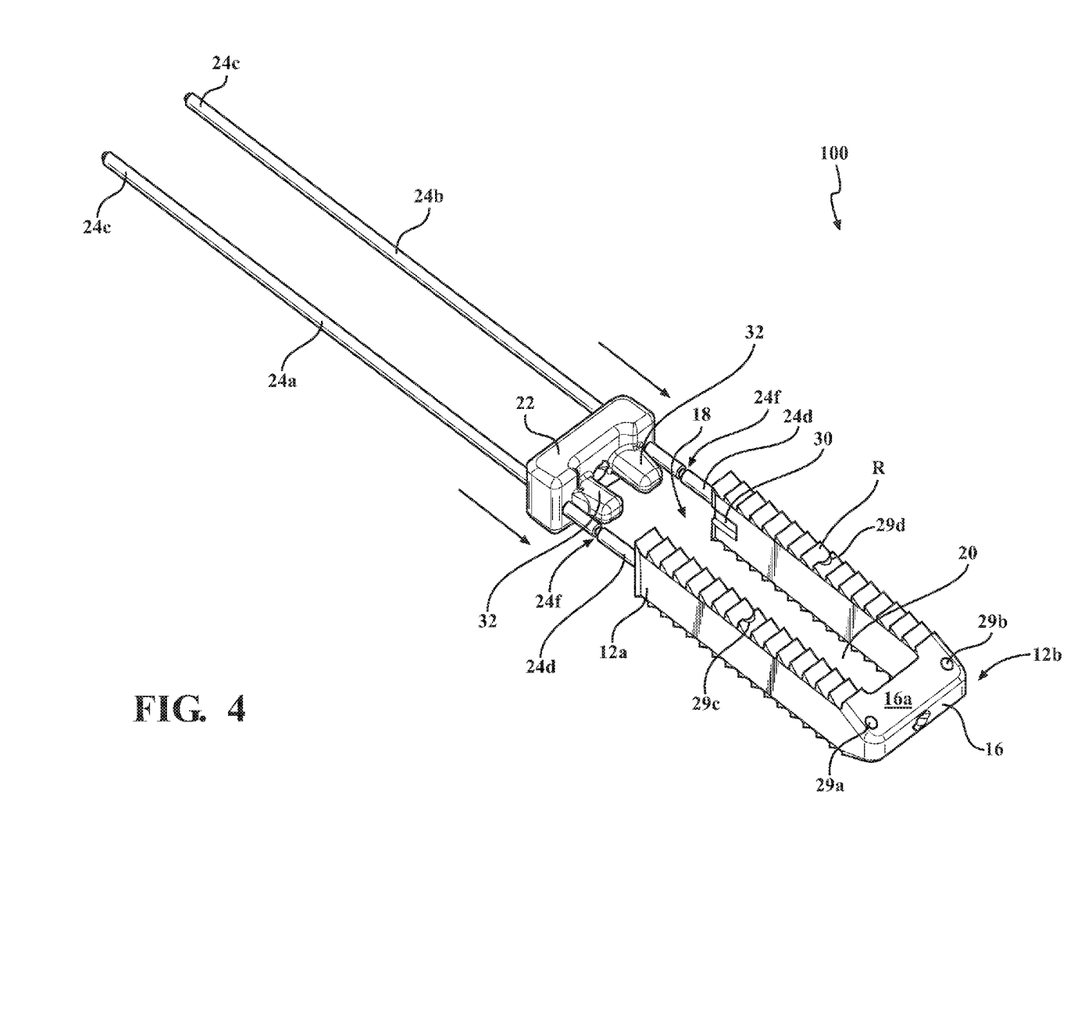
FIG. 4 depicts a partially exploded perspective view of a spinal implant according to one or more embodiments shown and described herein.

Now referring to FIGS. 1 and 4, an illustrative embodiment of a system 100 for implanting a spinal implant 10 between a pair of vertebra is provided. The spinal implant 10 has a main body 12. The main body 12 includes a proximal end 12a and a distal end 12b.

The main body 12 includes a pair of legs 14 and a nose 16 defining the distal end 12b of the main body. The legs 14 are spaced apart and generally parallel to each other and disposed on opposing sides of the nose 16 so as to form a generally U-shaped dimension having a top opening 18 and a cavity 20 defined by the pair of legs 14 and the nose 16. The cavity 20 is adapted to hold a filler material (not shown). The top opening 18 allows the surgeon to access the cavity 20. The surgeon may insert the filler through the top opening 18.

Each of the pair of legs 14 has an inferior and superior surface 14a, 14b. In one embodiment, the inferior and superior surfaces 14a, 14b include a plurality of ridges R so as to be generally ribbed. The nose 16 may be shaped to have a narrow front end so as to facilitate the introduction of the main body 12 between adjacent vertebrae. In particular, the nose 16 includes an angled surface 16a giving the distal end 12b of the main body 12 a tapered dimension to assist in insertion of the main body 12 between the vertebral bodies.

The system includes a cap 22. The cap 22 is configured to close the top opening 18. The proximal end 12a of the main body 12 is adapted to receive the cap 22. In one embodiment, the width of the cap 22 is generally the same as the width of the main body 12 such that the cap 22 covers the proximal end 12a of the main body.

The system 100 further includes an elongated member 24. In one embodiment, the system includes a pair of elongated members 24a, 24b. The proximal end 12a of the main body 12 further includes elongated members 24a, 24b. The elongated members 24a, 24b are mounted to the proximal end 12a of the main body 12. In particular, the elongated members 24a, 24b are mounted to apertures 26 disposed on the proximal end 12a of each of the legs 14 so as to extend away from the proximal end 12a of the main body 12. The elongated members 24a, 24b allow the cap to slide towards the main body 12 after the main body 12 has been implanted between a pair of vertebrae.

The elongated members 24a, 24b each include respective first ends 24c and respective second ends 24d. The first ends 24c of the elongated members 24a, 24b are proximal ends. The second ends 24d of the elongated members 24a, 24b are distal ends and connect directly to the main body 12. In one embodiment the second ends 24d are molded to or within the main body 12. Alternatively, the elongated members 24a, 24b may be inserted into the main body 12 in a press fit configuration, or formed as a one piece assembly. In such an embodiment, the second ends 24d of the elongated members 24a, 24b have a larger diameter than the aperture 26. In one embodiment, the elongated members 24a, 24b have second ends 24d having a larger diameter than the first ends 24c.

The elongated members 24a, 24b may be a wire or shaft, commonly made of a metal. The elongated members 24a, 24b may be solid or hollow depending on various requirements. Alternatively, the elongated members 24a, 24b may be made of a plastic material, similar to the plastic or polymer used to manufacture the main body 12 and the cap 22.

The main body 12 and the cap 22 are typically made of any implantable metal, such as titanium. In other embodiments, the main body 12 and the cap 22 are made from any implantable plastic or polymer material such as polyether ether ketone (PEEK) and the like.

FIGS. 1-6 illustrate a plurality of holes 28a, 28b, 28c, 28d. These holes 28a, 28b, 28c, 28d are configured to receive corresponding pins 29a, 29b, 29c, 29d. The pins 29a, 29b, 29c, 29d are made of any implantable metal to provide for visibility and locatability of the implant 100 on an X-ray. In a typical embodiment, the components of the main body 12, cap 22 and pins 29a, 29b, 29c, 29d are all made of a polymer or plastic material. Insertion of the pins 29a, 29b, 29c, 29d within respective holes 28a, 28b, 28c, 28d provide for visibility and location positioning of the spinal implant 10 on an X-ray. Positioning of the pins 29a, 29b, 29c, 29d is kept constant for each spinal implant to allow for uniform consistency between implants. Accordingly, the surgeon may view an x-ray machine to better understand the depth of the implant 10.

FIG. 4 depicts a partially exploded view of the spinal implant 10 before full installation of the cap 22. As illustrated by the directional arrows in FIG. 4, the cap 22 slides on respective elongated members 24a, 24b towards the main body 12 to securely connect with the main body 12. The elongated members 24a, 24b help guide the cap 22 to register with the top opening 18 of the main body 12. The cap 22 is installed after the filler or graft material has been inserted within the cavity 20.

Figure 6:
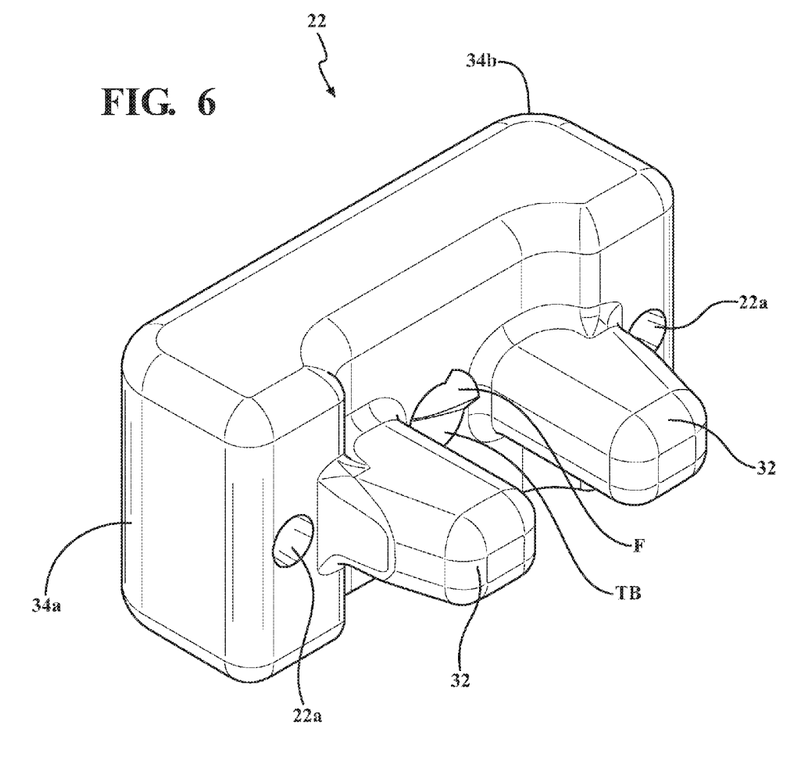
FIG. 6 depicts the cap according to one or more embodiments shown and described herein.
Figure 7:
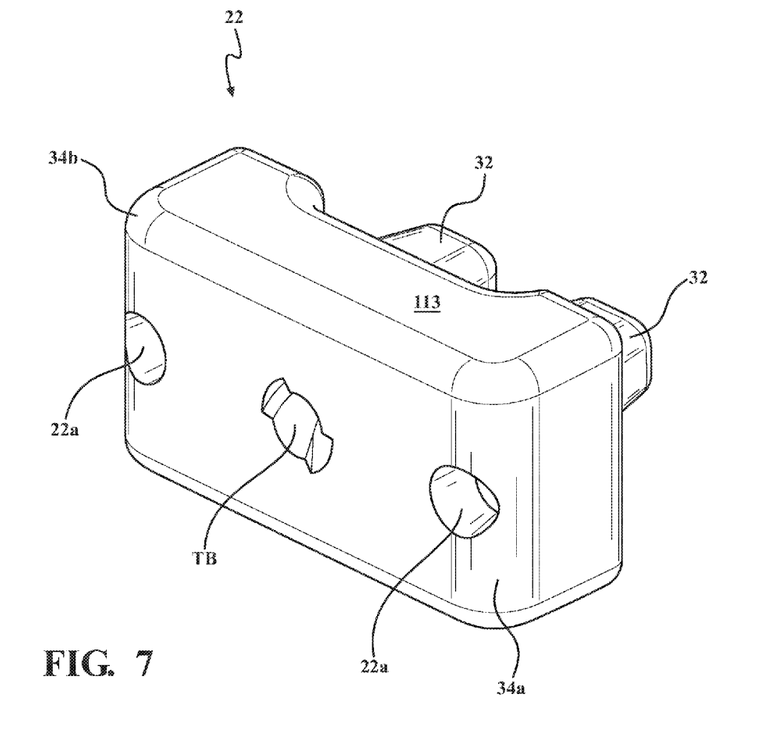
FIG. 7 illustrates an alternative perspective view of the cap according to one or more embodiments shown and described herein.
Figure 8:
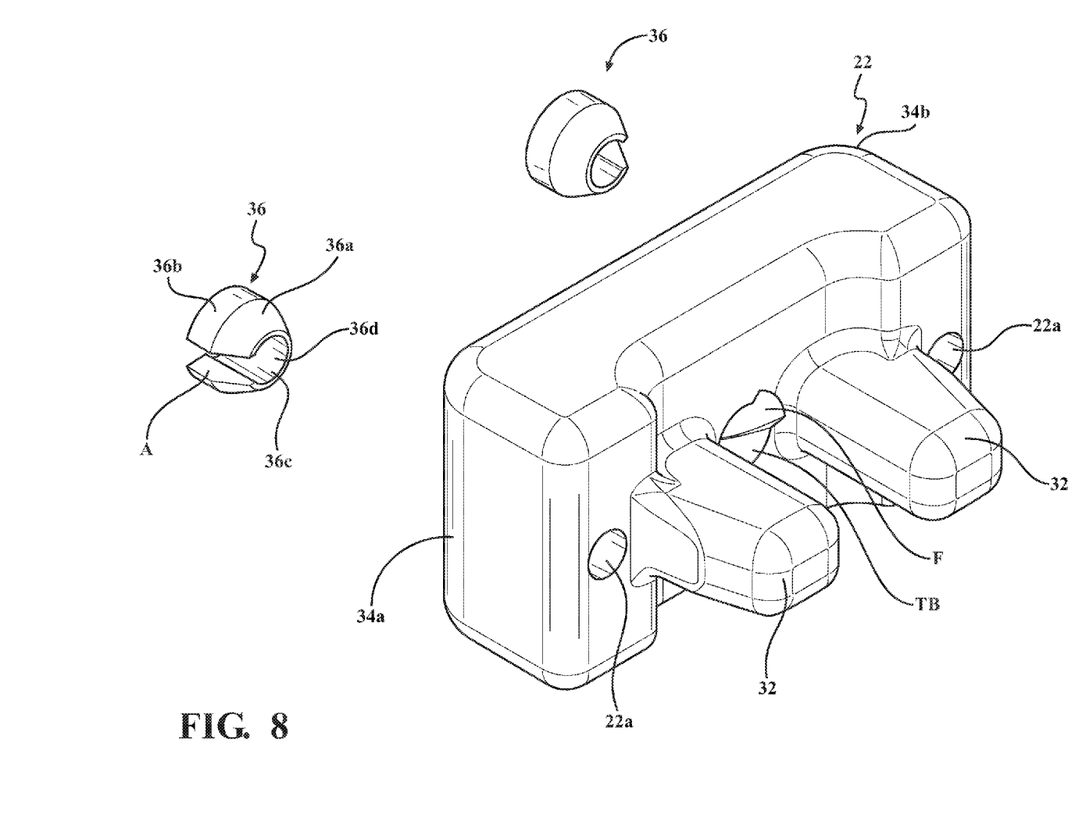
FIG. 8 illustrates an exploded view of the cap and securing members in a partially exploded perspective view according to one or more embodiments shown and described herein.

Now with reference to again to FIG. 4 and also FIGS. 6-8, the cap 22 further includes a through-hole 22a configured to slidingly receive an elongated member 24. For illustrative purposes the cap 22 is shown as having two through-holes 22a, each through-hole 22a is disposed on opposite sides of the cap 22 and extend from a top surface of the cap 22 to a bottom surface of the cap 22. Accordingly, the cap 22 may slide onto and along the elongated members 24a, 24b. The through-holes 22a, such as clearly illustrated in FIGS. 6-8, extend through the body of the cap 22. The cap 22 slides along the elongated members 24a, 24b until it reaches the main body 12 as shown in FIG. 1. In particular, the cap 22 is slid down the elongated members 24a, 24b so as to abut against the proximal end 12a of respective legs 14 of the main body 12.

Figure 5:
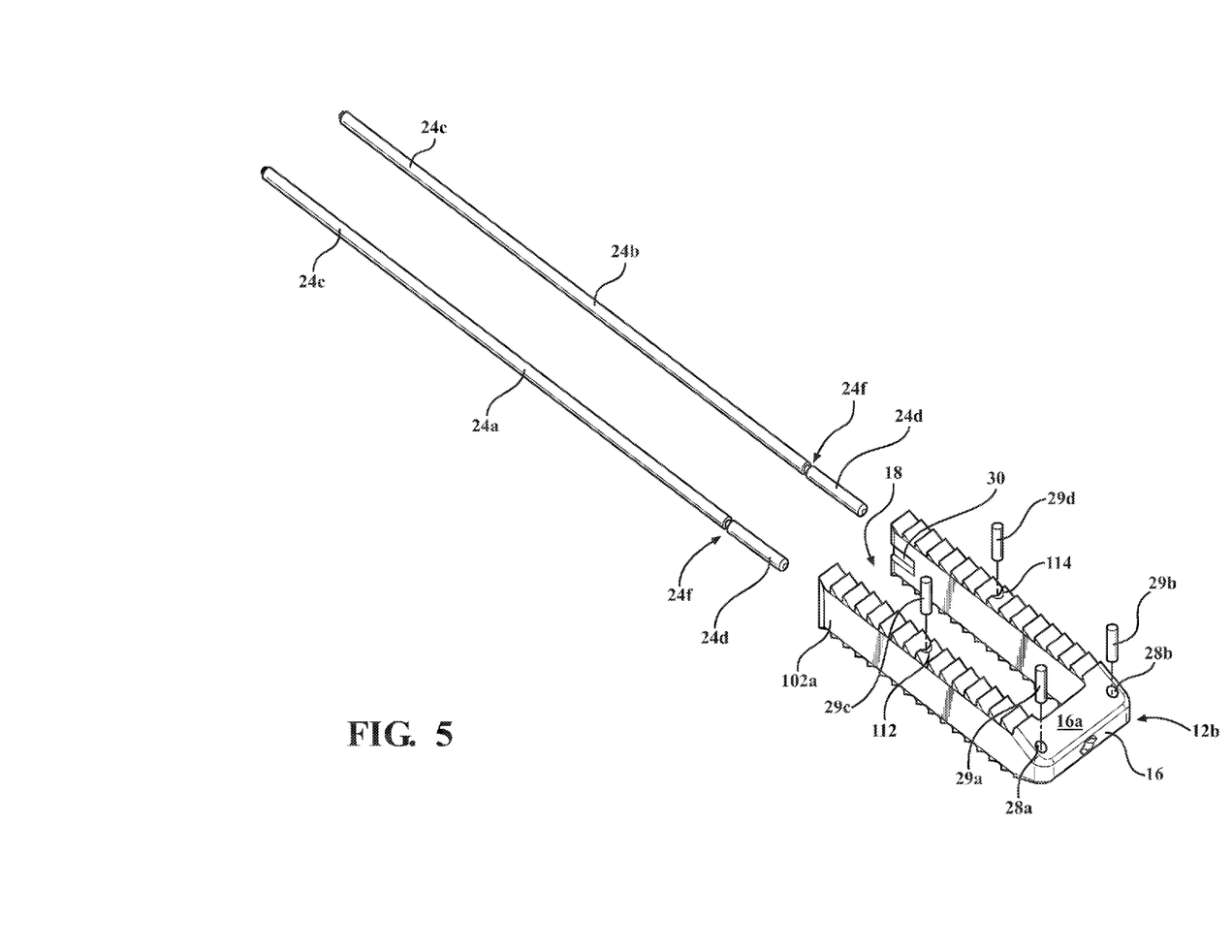
FIG. 5 depicts a partially exploded perspective view of the spinal implant according to one or more embodiments shown and described herein.
Figure 10:
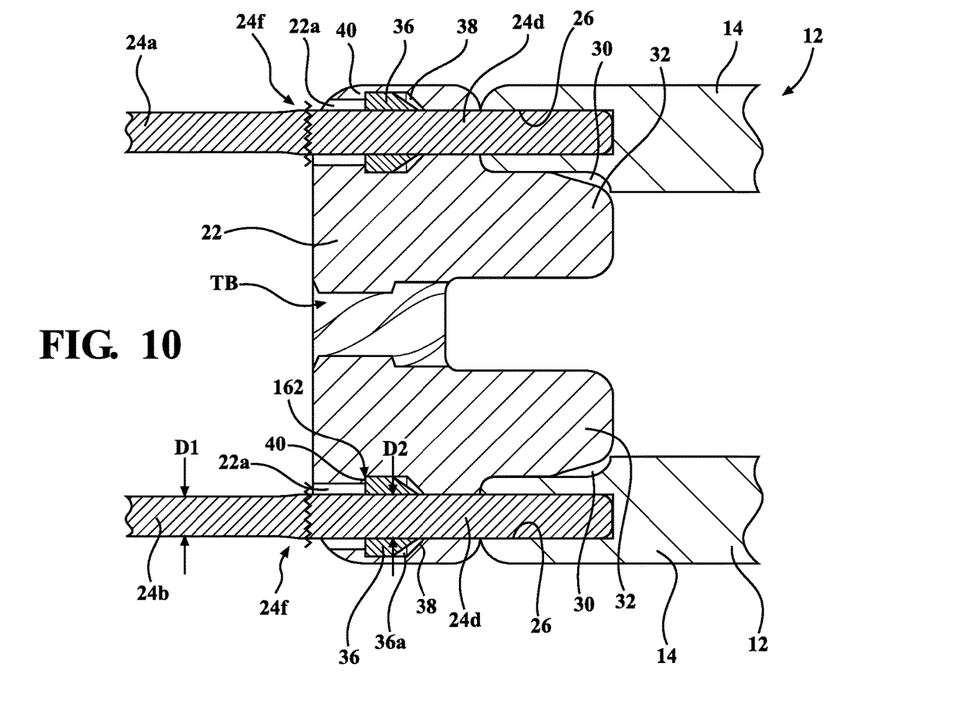
FIG. 10 illustrates a cross-sectional view of the spinal implant according to one or more embodiments shown and described herein.

In one embodiment, system 100 is configured to facilitate the registration of the cap 22 to the main body 12. In such an embodiment, the main body 12 may include an indentation 30 configured to help facilitate positioning of the cap 22 so as to help ensure the cap 22 is properly closed on the main body 12. FIGS. 4, 5 and 10 show an embodiment of the indentation 30. The indentation 30 is a recessed portion of an inner wall of the respective legs 14 disposed at the proximal end 12a of the main body 12. The indentation 30 is open to the top opening 18.

The cap 22 includes protrusions 32 disposed on the distal end of the cap 22. It should be appreciated that the cap 22 is illustratively shown as having two protrusions 32 disposed on opposite sides of the cap 22. The protrusions are configured to slide into respective indentations 30 so as to register the cap 22 with the main body 12. In other words, the protrusions 32 are seated within the indentations 30 so as to properly align the cap 22 with the main body 12. The protrusions 32 further provide for an increased surface area within the cavity 20 thereby pushing the filler material out of the cavity 20 to facilitate a better connection between the filler material and the vertebral bodies. The cap 22 is illustratively shown as having rounded corner portions 34a, 34b.

The cap 22 may further include threaded bore TB configured to receive a fastener F so as to connect the spinal implant 10 with a plate (not shown) positioned adjacent to the vertebral bodies. The threaded bore TB may also be adapted to connect to an inserter instrument (not shown) to aid in guiding the cap 22 along the elongated member 24a, 24b. Although the threaded bore TB is shown centrally located on the cap 22, it should be appreciated that the threaded bore TB may be positioned elsewhere so as to facilitate the connection of a plate or the actuation of an inserter instrument.

With reference now to FIG. 8, the system 100 further includes securement members 36, specifically illustrated as securement members 36. The securement members 36 are mounted within the cap 22 to permanently secure the cap 22 to the main body 12 by means of the elongated members 24a, 24b. Each of the securement members 36 include an angled outer surface 36a which is angled relative to a peripheral outer surface 36b. The peripheral outer surface has a generally constant radius relative to a center of a through-bore 36c. A corresponding inner surface 36d is provided and positioned in contact with the elongated members 24a, 24b when in an installed position. The securement members 36 may further include a radial opening A so as to define a generally C-shaped dimension.

Figure 9:
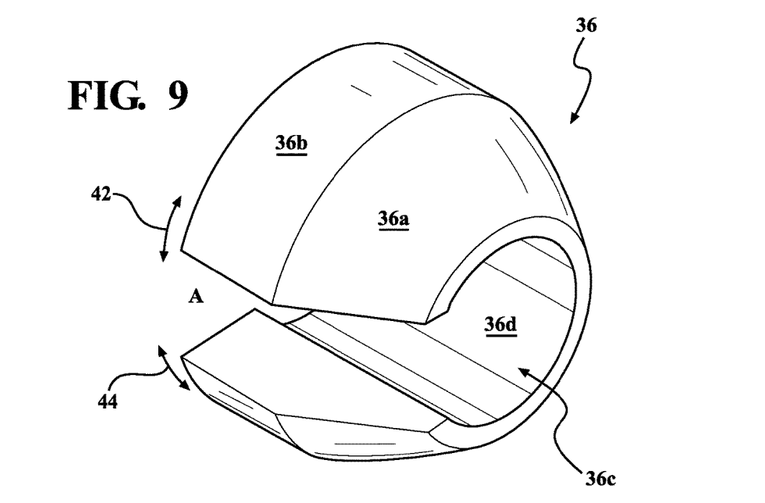
FIG. 9 depicts a perspective view of the securement member according to one or more embodiments shown and described herein.

FIG. 10 illustrates the securement members 36 in an installed position within the cap 22. The securement members 36 are installed within the through-holes 22a. The through-holes 22a extend through the length of the cap 22 thereby allowing the elongated members 24a, 24b to extend fully through the cap 22 to the main body 12. The through-holes 22a include a cavity 38 having a radius greater than a proximal portion of the through-hole 22a so as to form an inner ledge 40. The cavity 38 is configured to hold respective securement members 36. The securement members 36 are a one piece molded material made of any resilient and implantable plastic or polymer material. The radial opening A allows for a compressive spring action to act on the securement members 36, such as illustrated by directional arrows 42, 44, as illustrated in FIG. 9. Further, the radial opening A allows the ends of the securement member 36 to close onto each other, reducing the diameter of the securement member 36 so as to fit within the aperture 26. When the securement member 36 is disposed within the cavity 38, the resiliency of the securement member 36 opens the radial opening A wherein a back end of the securement member 36 is in direct contact with the inner ledge 40. Thus, it should be appreciated that the securement members 36 are formed of a resilient material suitable for medical implants.

When the securement members 36 are engaged with the elongated members 24a, 24b and disposed in a respective cavity 38, such as illustrated in FIG. 10, the securement members 36 facilitate a press fit connection between the cap 22 and the elongated members 24a, 24b.

In one embodiment, the elongated members 24 include tapered portions. In particular the first end 24c of the elongated members are narrow in diameter than the second end 24d so as to allow the cap 22 to easily slide on the elongated members 24 during installation. FIG. 10 illustrates the second end 24d of the elongated member 24 having a first diameter $D_1$ and the first end 24c of the elongated member 24 a second diameter $D_2$. The larger diameter at $D_2$ allows for a tighter press fit connection between the securement member 150a, the cap 22, the aperture 26, and the elongated members 24.

If a user attempts to remove the cap 22 from the main body 12, the compressive force of the securement member 36 will act on the elongated member 24a thereby preventing removal of the cap 22. If the user continues to pull on the cap 22 in an attempt to remove the cap 22 from the main body 12, the securement member 150a will continue to tighten around the elongated member 24a thus making removal of the cap 22 even more difficult. Further, the inner ledges 40 further facilitate the compressive force applied on the elongated members 24a, 24b if the user attempts to remove the cap 22. The inner ledges 40 also prevent the securement members 36 from backing out of the cap 22. The inner ledges 40 also encourage a slight cam force on the securement members 36 to even further enable the securement members 36 to exert a compressive force around the elongated members 24a, 24b.

After the cap 22 is installed and secured onto the main body 12, the surgeon then removes the elongated members 24a, 24b from the assembly by means of scissors, clamp, or other wire clipping means. FIG. 10 illustrates a weakening section 24f where the surgeon would remove the elongated members 24a, 24b from the assembly.

A method 200 of implanting a spinal implant 10 is also provided. The method 200 includes the step of inserting the main body 12 between adjacent vertebrae. The elongated members 24 may be inserted into the apertures 26 before or after the main body is inserted between the adjacent vertebrae. The cavity 20 is then filled with a filler such as a bone growth material. The cap 22 is then mounted onto an elongated member 24 or pair of elongated members 24, as the case may be. The cap 22 is slid along the elongated member 24 and mounted onto the main body 12 closing the top opening 20. The securement members 36 are then slid along respective elongated members 24 and pushed into respective apertures 26 until the securement members 36 are disposed in respective cavities 36. The elongated members 24 may then be broken off along a weakening section 24f.

It is noted that the terms "substantially" and "about" may be utilized herein to represent the inherent degree of uncertainty that may be attributed to any quantitative comparison, value, measurement, or other representation. These terms are also utilized herein to represent degree by which a quantitative representation may vary from a standard reference without resulting in a change in the basic function of the subject matter at issue.

While particular embodiments have been described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter. For instance, the cap may include a plurality of ridges disposed on the inferior and superior surfaces so as to help retain the cap between vertebral bodies.

The invention claimed is:

1. A system for performing a spinal procedure configured to introduce a filler between two vertebral bodies, the system comprising:
   a spinal implant having a main body adapted to rest between and adjacent to the two vertebral bodies, the main body having a pair of legs, a nose and a top opening so as to define a first cavity, the first cavity adapted to hold the filler, at least one of the legs having an aperture;
   an elongated member configured to fit within the aperture;
   a cap having a through-hole, the through-hole having a second cavity bound by the cap, the second cavity being larger in diameter than the through-hole so as to define an inner ledge; and
   a securement member having a through-bore and a radial opening that is open to and extends radially from the through-bore, the radial opening extending along a length of the through-bore, a portion of the elongated member disposed within the through-bore, the securement member adapted to fit entirely within the second cavity, the securement member made of a resilient material so as to generate a compressive force on the elongated member, wherein the compressive force closes the radial opening so as to reduce a diameter of the through-bore when the elongated member is pulled away from the cap, wherein the compressive force is actuated by the securement member being pressed against the inner ledge, the compressive force fixing the elongated member within the second cavity so as to connect the main body to the cap after the main body has been inserted between the vertebral bodies and after the filler has been inserted into the first cavity of the main body.

2. The system as set forth in claim 1, wherein the securement member includes an angled outer surface and a peripheral outer surface having a uniform radius relative a center of the through-bore.

3. The system as set forth in claim 2, wherein the elongated member is tapered from a distal end to a proximal end.

4. The system as set forth in claim 1, wherein one of the pair of legs includes an indentation, and wherein the cap includes a protrusion configured to engage the indentation so as to guide the coupling of the cap to the main body, and wherein the protrusion pushes the filler within the cavity.

5. A method of introducing bone growth material between two adjacent vertebrae, the method utilizing the system as set forth in claim 1, the method comprising the steps of:
   inserting the main body between the two adjacent vertebrae;
   filling the first cavity with the bone growth material;
   sliding the cap along the elongated member; and
   mounting the cap onto the main body so as to close the top opening;
   sliding the securement member along the elongated member and pushing the securement member into the aperture until the securement member is disposed in the second cavity.

6. The method as set forth in claim 5, wherein the elongated member is broken off along a weakening section.

7. The method as set forth in claim 5, wherein the elongated member is inserted into the aperture before the main body is inserted between the two adjacent vertebrae.

8. The method as set forth in claim 7, wherein the cap includes a protrusion configured to push the bone growth within the first cavity and into contact with the two adjacent vertebrae.

9. The method as set forth in claim 8, wherein one of the pair of legs includes an indentation, and wherein the protrusion is configured to engage the indentation so as to guide the coupling of the cap to the main body.

10. A spinal implant for positioning between two vertebral bodies, the spinal implant adapted to hold a filler, the spinal implant comprising:
    a main body adapted to rest between and adjacent to the two vertebral bodies, the main body having a pair of legs and an end wall so as to define a first cavity, the first cavity adapted to hold the filler, each of the pair of legs having an aperture;
    a pair of elongated members configured to slide within the bore of a corresponding one of the pair of legs; and
    a cap having a pair of through-holes and a pair of securement members, each of the pair of through-holes includes a second cavity bound by the cap, the second cavity being larger in diameter than the respective through-hole so as to define an inner ledge, each of the pair of securement members having a through-bore and a radial opening that is open to and extends radially from the through-bore, the radial opening extending along a length of the through-bore, and each of the pair of securement members is adapted to fit entirely within a respective second cavity, the pair of securement members made of a resilient material so as to generate a compressive force on a respective elongated member, wherein the compressive force closes the radial opening so as to reduce a diameter of the through-bore when the elongated member is pulled away from the cap, wherein the compressive force is actuated by the securement member being pressed against the inner ledge, the compressive force fixing the respective elongated member within the respective second cavity so as to connect the main body to the cap after the main body has been inserted between the vertebral bodies and after the filler has been inserted into the first cavity of the main body.

11. The spinal implant as set forth in claim 10, wherein the pair of through-holes is registered with a respective aperture of pair of legs when the cap is mounted to the main body.

12. The spinal implant as set forth in claim 10, wherein each of the pair of securement members includes an angled outer surface and a peripheral outer surface having a uniform radius relative the a center of the through-bore.

13. The spinal implant as set forth in claim 12, wherein each of the pair of elongated members is tapered from a distal end to a proximal end.

14. The spinal implant as set forth in claim 10, wherein one of the pair of legs includes an indentation, and wherein the cap includes a protrusion configured to engage the indentation so as to guide the coupling of the cap to the main body, and wherein the protrusion pushes the filler within the cavity.

* * * * *